(12) United States Patent
Gross et al.

(10) Patent No.: US 9,053,583 B1
(45) Date of Patent: Jun. 9, 2015

(54) SYSTEM AND METHOD FOR PROVIDING INTELLIGENT PARAMETER SUBSTITUTIONS FOR CLINICAL APPLICATIONS

(75) Inventors: Brian David Gross, North Andover, MA (US); Soren Steiny Johnson, Wakefield, MA (US); Elizabeth J. Zengo, Hudson, NH (US); David Youngjin Kim, Roxbury Crossing, MA (US); Dmitri Shvartsman, Belmont, MA (US); Gregory Raber, Sterling, MA (US)

(73) Assignee: Koninklijke Philips N.V., Eindhoven (NL)

( * ) Notice: Subject to any disclaimer, the term of this patent is extended or adjusted under 35 U.S.C. 154(b) by 67 days.

(21) Appl. No.: 13/995,308

(22) PCT Filed: Dec. 14, 2011

(86) PCT No.: PCT/IB2011/055658
§ 371 (c)(1),
(2), (4) Date: Jun. 18, 2013

(87) PCT Pub. No.: WO2012/085762
PCT Pub. Date: Jun. 28, 2012

Related U.S. Application Data

(60) Provisional application No. 61/425,985, filed on Dec. 22, 2010.

(51) Int. Cl.
| G06T 11/00 | (2006.01) |
| G06T 11/60 | (2006.01) |
| G06Q 50/24 | (2012.01) |
| G06F 19/00 | (2011.01) |
| G06T 11/20 | (2006.01) |

(52) U.S. Cl.
CPC .............. *G06T 11/60* (2013.01); *G06T 11/206* (2013.01); *G06Q 50/24* (2013.01); *G06F 19/3406* (2013.01); *G06F 19/3487* (2013.01); *G06F 19/345* (2013.01); *G06F 19/327* (2013.01)

(58) Field of Classification Search
CPC .............. G06F 19/327; G06F 19/3406; G06F 19/3487; G06F 19/322; G06F 19/325; G06Q 50/24; G06Q 50/22; G06Q 10/10
USPC .............. 345/636, 637, 440, 440.1; 600/300; 705/2, 3
See application file for complete search history.

(56) References Cited

U.S. PATENT DOCUMENTS

| 2009/0054743 A1 | 2/2009 | Stewart |
| 2010/0168544 A1 | 7/2010 | Kamath et al. |

(Continued)

FOREIGN PATENT DOCUMENTS

| WO | 2010091073 A2 | 8/2010 |
| WO | 2010102069 A2 | 9/2010 |

OTHER PUBLICATIONS

Burykin, A., et al.; Toward optimal display of physiologic status in critical care: I. Recreating bedside displays from archived physiologic data; 2010; Journal of Critical Care; 9 pages.

*Primary Examiner* — Jin-Cheng Wang

(57) ABSTRACT

A patient monitoring station (44) includes a display (12) that displays a plurality of sectors (60), each sector including one or more tiles (64). A controller (46) displays patient data received from a patient information server (10) in a corresponding sector of the display. The controller is programmed to populate the tiles of the sectors with patient data according to a selected clinical theme.

19 Claims, 11 Drawing Sheets

(56) References Cited

U.S. PATENT DOCUMENTS

| | | |
|---|---|---|
| 2010/0198314 A1 | 8/2010 | Wei |
| 2010/0198622 A1 | 8/2010 | Gajic et al. |
| 2011/0001605 A1* | 1/2011 | Kiani et al. .................... 340/5.6 |
| 2011/0077968 A1* | 3/2011 | Kelly et al. ....................... 705/3 |
| 2011/0105854 A1* | 5/2011 | Kiani et al. .................... 600/300 |
| 2012/0239420 A1* | 9/2012 | Stapelfeldt et al. ............... 705/2 |

* cited by examiner

SYSTEM AND METHOD FOR PROVIDING INTELLIGENT PARAMETER SUBSTITUTIONS FOR CLINICAL APPLICATIONS

CROSS REFERENCE TO RELATED APPLICATIONS

This application is a national filing of PCT application Serial No. PCT/IB2011/055658, filed Dec. 14, 2011, published as WO 2012/085762 A2 on Jun. 28, 2012, which claims the benefit of U.S. provisional application Ser. No. 61/425,985 filed Dec. 22, 2010, which is incorporated herein by reference.

The present application relates to medical monitoring and clinical data display devices for monitoring the physiological condition of a patient. It finds particular application in improving the configuration and accessibility of patient information on a patient monitor, central monitoring system, bedside monitor, or mobile monitoring display and will be described with particular reference thereto.

Presently, central station or other multi-patient monitoring devices have a fixed area or sector of a display assigned to each patient. The monitoring sectors include a plurality of tiles which display various types of patient information. Each sector typically is populated by several tiles that display the patient's identification, patient status, alarms, physiological parameters, such as an EGG signal, a respiration signal, pulse rate, blood pressure, SpO2, other indicators of patient health or well being, and the like. As more physiological parameters are monitored, the displayed information is typically compressed or displayed in a smaller, harder to read size or the like in order to fit in the fixed sector assigned to the patient. The sectors and tiles of the central station or other multi-patient monitoring devices can also be configured by a clinician; by configuration, the system can require that for significant changes, the device needs to be placed in a configuration mode, after which the sectors and tiles remain largely fixed. As patient physiological parameter measuring devices become more widely available, more and more physiological parameters are being measured for each patient.

The present application provides a new and improved patient monitoring device which overcomes the above-referenced problems and others.

In accordance with one aspect, a patient monitoring station is provided. The patient monitoring station is comprised of a display that displays a plurality of sectors, each sector including one or more tiles. A controller displays patient data received from a patient information server in a corresponding sector of the display. The controller programmed to or including means to populate the tiles of the sectors with patient data according to a selected clinical theme.

In accordance with another aspect, a method of displaying medical parameters is provided. The method comprising controlling a display to display patient data received from a patient information server in a corresponding sector of a display, populating one or more tiles of the sector with the patient data according to a selected clinical theme, and optimizing the layout of the sector by displaying the tiles populated with patient data according to the selected clinical theme.

One advantage resides in the automatic and real-time optimization of the layout of patient information on a patient monitoring device.

Another advantage resides in utilization of dynamic sector layouts.

Another advantage resides in reduction of screen clutter and distractions from nonessential patient information.

Another advantage resides in easier readability of patient information on a patient monitoring device.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
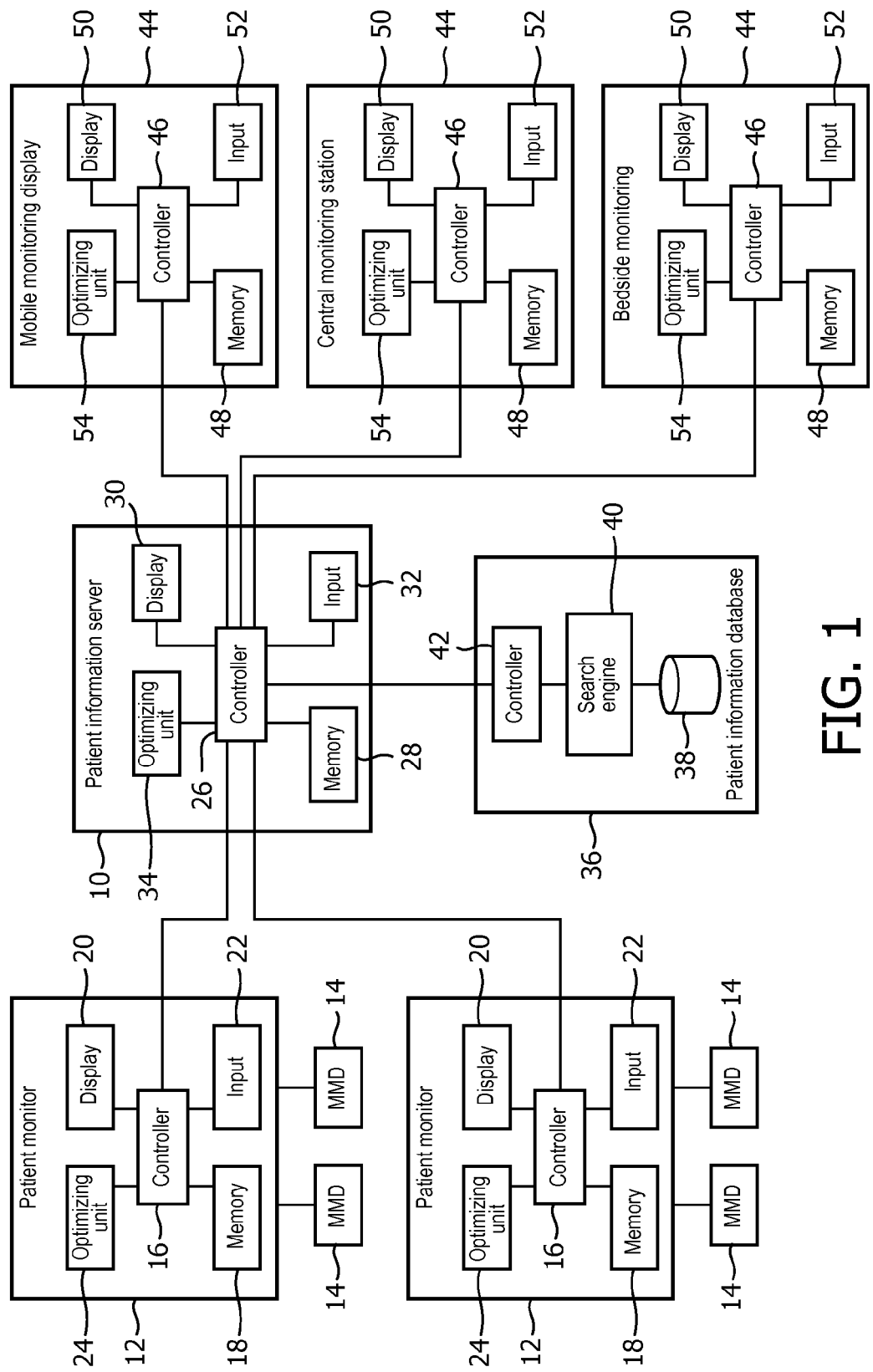
FIG. 1 is a diagrammatic illustration of a patient monitoring system in accordance with the present application.

With reference to FIG. 1, a patient information server 10 receives physiological data from a plurality of multi-functional patient monitor devices (PMD) 12 that monitor assigned patients (not shown) by various medical monitoring devices or sensors 14. The medical monitoring devices 14 measure physiological parameters of the patient and generate the physiological data indicative thereof. These medical monitoring devices 14 may include an electrocardiographic (ECG) instrument with ECG electrodes, IV fluid pumps, blood pressure sensors, SpO2 sensors, pulse sensors, thermometers, respiratory sensors, exhaled gas sensors, and the like. Other medical monitoring devices 14 can be associated with a patient, and not all of the above-mentioned medical monitoring devices 14 have to be associated with a patient at any given time. It should be appreciated that while only two patient monitors 12 and medical monitoring devices 14 are illustrated, more patient monitors and medical monitoring devices are contemplated. As used herein, medical monitoring devices signifies data sources indicating patient health, or the like. Electronics for receiving signals from the medical monitoring device 14 and for optionally performing signal processing on such signals are embodied in the illustrated embodiment as a multi-functional patient monitor device (PMD) 12, or may be embodied partly or wholly as on-board electronics disposed with one or more of the medical monitoring devices 14 or so forth. It should also be appreciated that the medical monitoring devices 14 and the PMD 12 could also be embodied into a single device. The PMD 12, for example, may be a monitor or monitoring system that travels with the patient, such as the transmitter of an ambulatory patient worn monitoring system, or the like.

In one embodiment, the medical monitoring devices 14 transmit the generated physiological data via a body coupled network, Bluetooth, wired or wireless network, or the like to a controller 16 of the PMD 12. The PMD 12 serves as a gathering point for the physiological data measured by the medical monitoring devices 14 and provides temporary storage for the data in a memory 18. The collected physiological data is concurrently transmitted to a controller 16 in the PMD 12 which then transmits the physiological data through a hospital network (not shown) to the patient information server 10 where the physiological data is displayed and stored. The controller 16 of the PMD 12 also controls a display 20 to display the measured physiological data received from each of the medical monitoring devices 14 in the corresponding PMD display 20. The controller 16 also optimizes the layout of the display 20 using one or more dynamic sector layouts described in further detail below. The dynamic sector layouts utilize defined rules to layout sectors of the display 20 based on the size of the sectors, the resolution and size of the display 20, the patient data available, and a user selected clinical theme. The selected clinical theme allows the user to populate the sector with certain tiles that specifically relate to a certain body system, disease, concept of interest, progression of disease or recovery, and the like. Optionally, an optimizing unit 24 optimizes the layout of the display using the one or more dynamic sector layouts. The PMD 12 also includes an input device 22 that allows the user, such as a system administrator, to view, manipulate, select clinical themes and/or interact with the data displayed on the display 20. The input device 22 can be a separate component or integrated into the display 20 such as with a touch screen monitor.

A controller 26 of the patient information server 10 receives the physiological data from the PMDs 12 and stores the physiological data in a memory 28. The controller 26 then controls a display 30 of the patient information server 18 to display the physiological data received from the patient in the display 30. The controller 26 can also optimize the layout of the display 30 using one or more dynamic sector layouts described in further detail below. The dynamic sector layouts utilize defined rules to layout sectors of the display 30 based on the size of the sectors, the resolution and size of the display 30, the patient data available, and a user selected clinical theme. Optionally, an optimizing unit 34 optimizes the layout of the display using the one or more dynamic sector layouts. The patient information server also includes an input device 32 that allows the user, such as administrative personal, to view, manipulate, select clinical themes, and/or interface with the data displayed on the display 30. The input device 32 can be a separate component or integrated into the display 30 such as with a touch screen monitor.

In one embodiment, the measured physiological data is transmitted and stored in a patient information database 36. The measure physiological data is stored in a patient case or study. The patient information database includes a patient database 38 for storing historical patient cases and studies including past patient data fields. The past patient data fields include one or more vital signs (including heart rate, blood pressure, respiration rate, oxygen saturation, body weight, other blood pressures, and the like), automated or user-input problem lists including chronic problems, acute admitting problems (chest pain, shortness of breath, altered mental status/confusion, abdominal pain, and the like), ICD-9 codes (or equivalent coded medical problems), clinical laboratory data, fluid-balance, medications, ventilator settings, subjective nursing assessment, results of imaging studies, patient demographics (age, gender, race/ethnic background), current time of stay in the hospital or ICU, and the like relating to patient cases and studies. A search engine 40 searches the patient database 38 for historical patient cases and studies to find correlations to requested patient cases and studies. The requested patient cases and studies are inputted by the user through the input device 32 of the patient information server 10. The correlating patient cases and studies are then transmitted as historical data by a controller 42 of the patient information database 36 to the controller 26 of the patient information server 10 where the historical data is stored. The controller 26 also controls and optimizes the display 30 of the patient information server 18 to display the historical data received from the patient information database 36 using one or more dynamic sector layouts described in further detail below.

In another embodiment, the physiological data and historical data stored in the patient information server 10 are transmitted to a plurality of patient information display systems 44. The patient information display systems 44 monitor a plurality of patients, e.g. in a centralized, multi-patient clinical display station. For example, a nurse may view a plurality of patient's physiological data and historical data on the patient's bedside monitor, another patient's bedside monitor, a central monitoring station, a mobile monitoring display, a PDA, or the like. It should be appreciated that while only three patient information displays 44 are illustrated, more patient information displays are contemplated. A controller 46 of each of the patient information display systems 44 receives the physiological data and historical data from the patient information server 10 and stores the physiological data and historical data in a memory 48. The controller 46 also receives clinical theme or information from which the theme can be inferred, e.g. diagnosis, ICD9 codes, location (intensive care, surgery, recovery, or the like), and the like. The controller 46 then controls a display 50 of the patient information display system 44 to display the physiological data and historical data received in the display 50. The controller 46 can also optimize the layout of the display 50 using one or more dynamic sector layouts described in further detail below. The dynamic sector layouts utilize defined rules to layout sectors of the display 50 based on the size of the sectors, the resolution and size of the display 50, the patient data available, and a user selected clinical theme. Optionally, an optimizing unit 54 optimizes the layout of the display using the one or more dynamic sector layouts. The patient information display systems 44 also includes an input device 52 that allows the user, such as administrative personal, to request historical patient cases and studies, to view, manipulate, select clinical themes, and/or interface with the data displayed on the display 50. The input device 52 can be a separate component or integrated into the display 50 such as with a touch screen monitor. It should also be appreciated that the PMD 12 and the patient information server 10 are patient information display systems that receives and display the physiological data and historical data stored in the patient information server 10.

The patient monitors 12, patient information server 10, patient information database 36, and the patient information display systems 44 each include a processor, for example a microprocessor or other software controlled device configured to execute patient monitoring software for performing the operations described in further detail below. Typically, the patient monitoring software is carried on non-transitory tangible memory or a computer readable medium for programming of or execution by the processor. Types of computer readable media include memory such as a hard disk drive, CD-ROM, DVD-ROM and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 2:
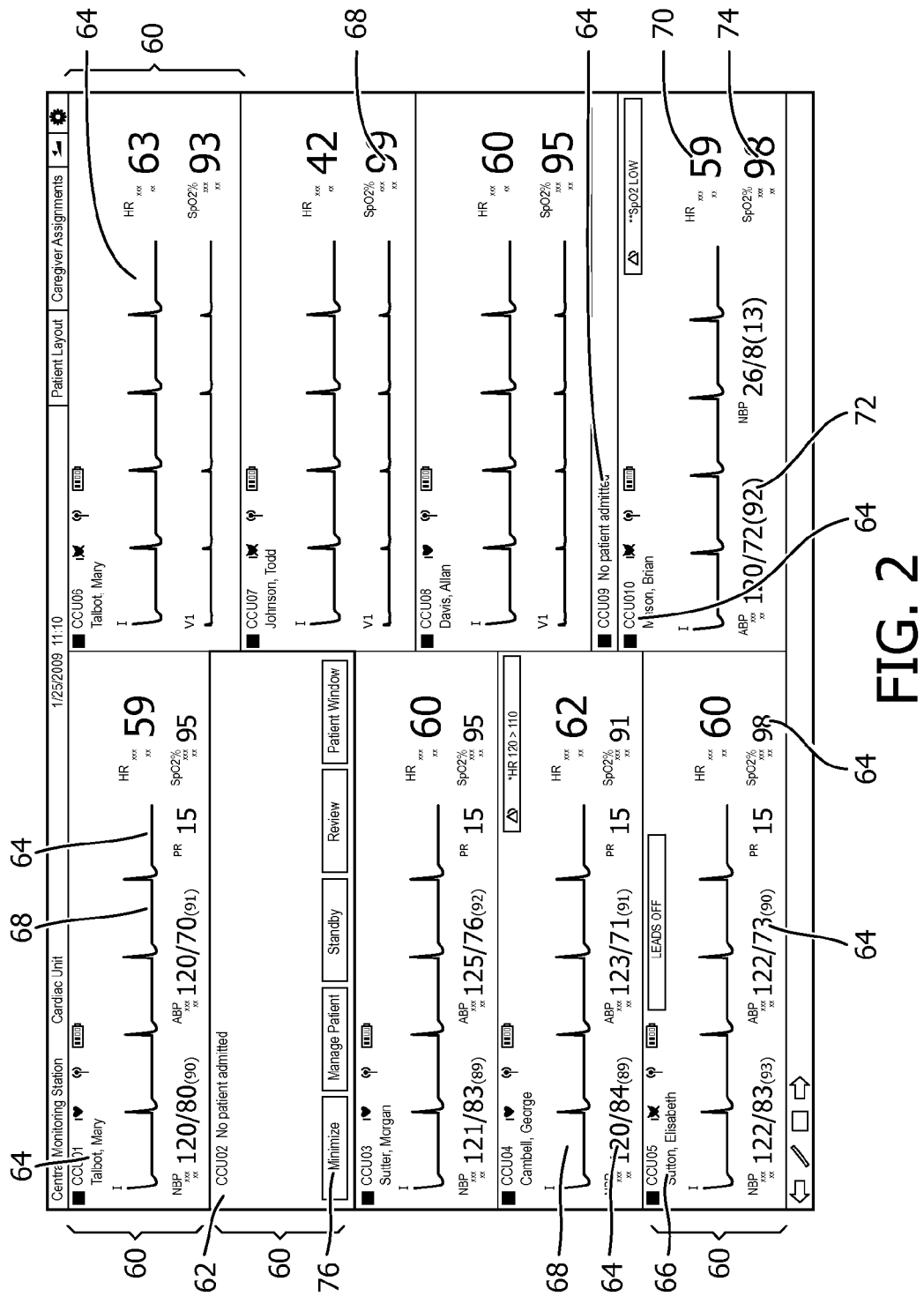
FIG. 2 illustrates an example of a ten sector display of a patient information display system in accordance with the present application.

As mentioned previously, controllers 16, 26, 46 direct the displays 20, 30, 50 of the patient information display systems 10, 12, 44 to display the physiological data and historical data stored in the patient information server 10. With reference now to FIG. 2, a display 20, 30, 50 of a patient information display system 44 is divided into sectors 60, each sector 60 representing information received from or corresponding to one patient. It is also contemplated that each sector 60 can represent information corresponding to one historical patient case or study. Ten sectors 60 are illustrated in FIG. 2, but more or fewer sectors are also contemplated. The number and size of sectors 60 per patient information display system 44 could be dictated by the size of the display 20, 30, 50, the patient to patient information display system 10 ratio, the number of patients, and other factors. As illustrated, each of the sectors 60 of the display 20, 30, 50 corresponds to one patient. Physiological data or historical data associated with each patient or patient case or study is displayed within the corresponding sector 60. When no patient is admitted to a specific bed, a hospital patient administration system advices the patient information display system 44 not to expect to receive information from the patient information server 10 to which no patient is assigned and a message 62 is displayed indicating that no patient is admitted.

The sectors 60 of the display 20, 30, 50 include a plurality of tiles 64 corresponding to the physiological and historical data received from the patient information server 10. For example, the sector 60 includes a patient ID tile 66 where the patient's name, bed or room number, assigned patient group, caregiver or team, and other identifying information, such as a unique hospital ID are displayed. An ECG tile 68 displays the latest ECG readings received from the patient information server 10 about the patient. A pulse tile 70 displays the latest pulse rate readings of the patient. A blood pressure tile 72 displays the latest blood pressure reading from the patient. There may also be a SpO2 tile 74, end tidal CO2 (etCO2) tiles, respiration tiles, alarm tiles, waveform tiles, a ST map tile, trend tiles, other physiological data tiles, historical data tiles, a battery life tile, and the like. Other tiles 64 can be associated with a sector 60, and not all of the above-mentioned tiles 64 have to be associated with a sector 60 at any given time.

The controllers 16, 26, 46 automatically optimize the layout of the sectors 60 of the displays 20, 30, 50 of the patient information display systems 44 using dynamic sector layouts. The dynamic sector layout utilizes the available data types, the clinical theme, and display 20, 30, 50 resolution and size to optimize the layout of the tiles 64 within the sector 60. Instead of the tiles within a sector having a fixed size and placement for the data, the dynamic layout utilizes defined rules to layout the sector 60 based on the size of the sector 60, the physiological and historical data available, user preference, and the selected clinical theme. The selected clinical theme allows the sector 60 to be populated with certain tiles 64 that specifically relate to a certain body system, disease, concept of interest, treatment, and the like. For example, if the user would like to display information relating to a patient's blood pressure, the user could select the blood pressure clinical theme and the controller 16, 26, 46 would automatically populate the sector with tiles that relate or are relevant to the patient's blood pressure rather than having to manually configure the sector with the relevant tiles. The tiles can also be populated based on a clinical theme related to a treatment, for example an anesthesia data view would include respiratory gas tile as well as ventilator data tile coming from different devices or device interfaces to create an anesthesia data view. The user could also select clinical themes for heart attaches recovery, cardiac surgical preparation, cardiac surgery, cardiac surgery recovery, convalescence as well as themes based on other medical conditions, other affected organs, other stages of treatment, other types of treatments, and the like. Once the clinical theme is selected, the controller 16, 26, 46 determines what physiological or historical data is available from the patient information server 10 and populates the sector with tiles that are most relevant to the selected clinical theme and displays the more important tiles larger, more prominently, and the like. For example, if the user selected the blood pressure clinical theme, the controller 16, 26, 46 would determine what physiological parameters were being monitored or what historical parameters were monitored and select the best available tiles relating to blood pressure to populate the sector.

To enable user interfacing, selection of clinical themes, and the exchange of monitored physiological data, in addition to the display 20, 30, 50, the patient information display system can also include a sector user interface or an input/output (I/O) portion 76 for each sector 60. The sector user interface 76 allows the user to select a clinical theme and/or view and/or manipulate the data of each sector 26 displayed on the display 18, e.g. a touch screen display. Alternatively, the patient information display system optionally incorporates a keypad, keyboard, touch sensitive screen, or other user input device (not shown) to enable user input.

The controller 16, 26, 46 optimizes the layout of a sector 60 by populating the sector 60 with certain tiles 64 that specifically relate to the clinical theme in real-time. The controller 16, 26, 46 selects the tiles 64 based on a tile prioritization for each of the clinical themes. For each clinical theme, a series of tile allocations are prioritized in a look-up table. The controller 16, 26, 46 determines what physiological and historical data is available and associates the best parameters with the tile allocation of the clinical theme. If the controller determines that no data exists for a tile to be allocated the controller determines if the next prioritized tile can be allocated. For example, in a clinical theme that allocates the first prioritized tile as heart rate and a second prioritized tile as blood pressure, the controller 16, 26, 46 will assign the best parameter available which indicates heart rate to the heart rate tile. Pulse rate, for example, can come from various sources, such as an ECG signal, an SpO2 signal, a blood pressure signal, and the like. The next tile assigned to the sector would be the best available parameter depicting the patient's blood pressure. As more space in the sector becomes available the more tiles from the prioritized look-up table are displayed. When space in the sector is reduced, the controller 16, 26, 46 removes tiles from the sectors based on the prioritized look-up table. The prioritized look-up table includes numeric tiles, trend tiles, wave tiles and the like. For example, a cardiac theme clinical theme can include specific tiles associated with ECG wave form, ST map, ST snippets, specific lab values, and the controller 16, 26, 46 will use the theme to allocate optimal ones and an optimal number of those tiles for the sector space available.

Along with determining what tiles 64 are allocated to the sector 60, the controllers 16, 26, 46 also determine the size of the tiles 64. The controller 16, 26, 46 changes the size of the various tiles 64 in order to optimize the space available in the sector 60 and the visibility of the higher priority information for the theme. Each tile 64 has a maximum and minimum size that allows the controller to determine the layout of the sector 60. The controller 16, 26, 46 uses the minimum values of the prioritized tiles of a clinical theme to calculate the maximum number of tiles which can be allocated to a sector. For example, if the prioritized look-up table of tiles in a clinical theme consists of a primary wave tile, ST map tile, and a trending tile, the controller 16, 26, 46 will assign the primary wave tile to the sector tile. If it is determined that the minimum size of the primary wave tile and the minimum size of the ST map tile is greater than the size available the controller will only assign the primary wave tile to the sector. If the space available is only large enough to allocate the minimum size of the primary wave tile and the ST map tile, then the controller 16, 26, 46 will allocate both those tiles but not allocate the trending tile. If the space available is large enough to allocate the minimum size of all three tiles then all three tiles will be assigned to the sector. It is contemplated that the sector could be minimized to one tile displaying the bed label or heart rate. If all of the available data is displayed and the sector is not full, the size of some of all of the tiles can be enlarged with preference being given to higher priority information.

It is also contemplated that a duration displayed, e.g. number of cardiac cycles on a ECG graph, on a the tile be in specific increments, e.g. even divisors of 60 so that the clinician can calculate per minute information easily. The controller can also optimize the size of the tile based on the amount of information stored. If the amount of information stored is less than a default time span then controller can expand the tile in order to properly display the data. The controller 16, 26, 46 also can control the tiles to display specific colors and icon representations for patient group, care group, etc. For example, if it is determined that the patient has been moved outside the care unit, the controller 16, 26, 46 will minimize the sector because the parameters of the patient would no longer need to be monitored in the present care unit.

Figure 3:
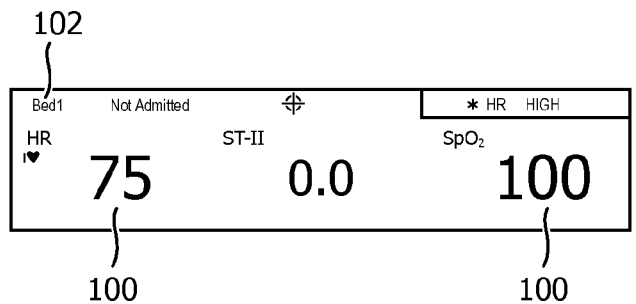
FIGS. 3-5 illustrate examples of numeric-only sectors of a patient information display system in accordance with the present application.
Figure 4:
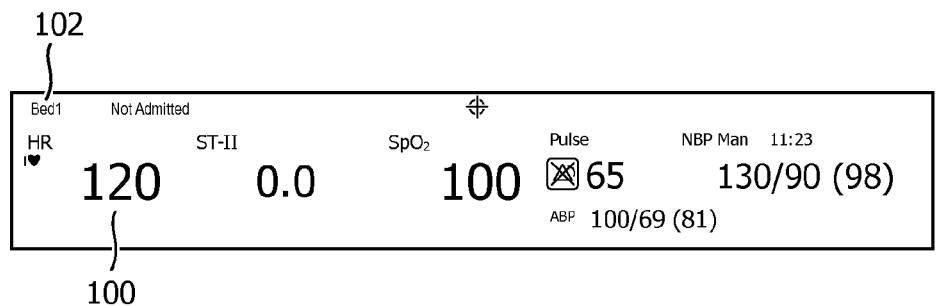
Figure 5:
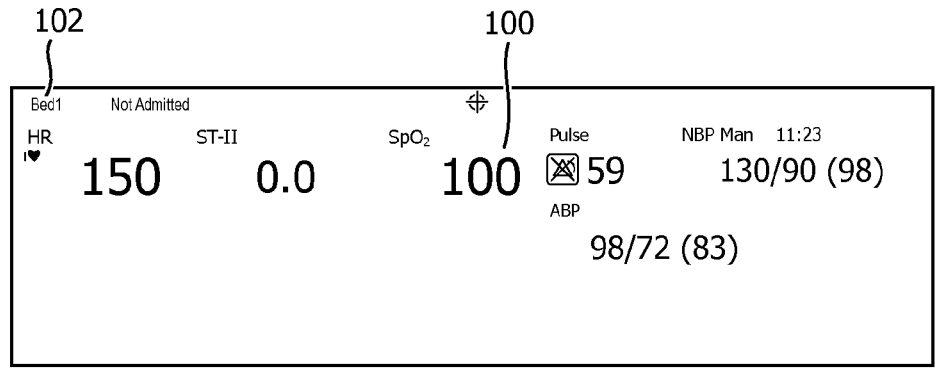
Figure 6:
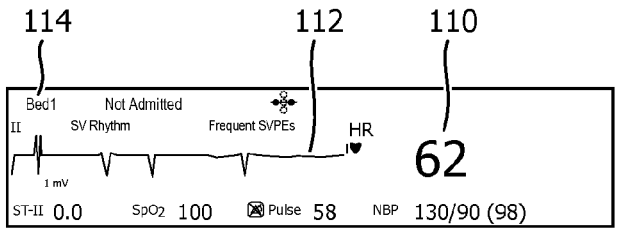
FIG. 6-9 illustrate examples of basic view sectors of a patient information display system in accordance with the present application.
Figure 7:
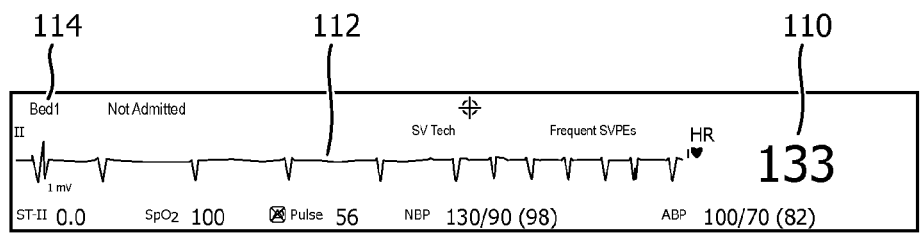
Figure 8:
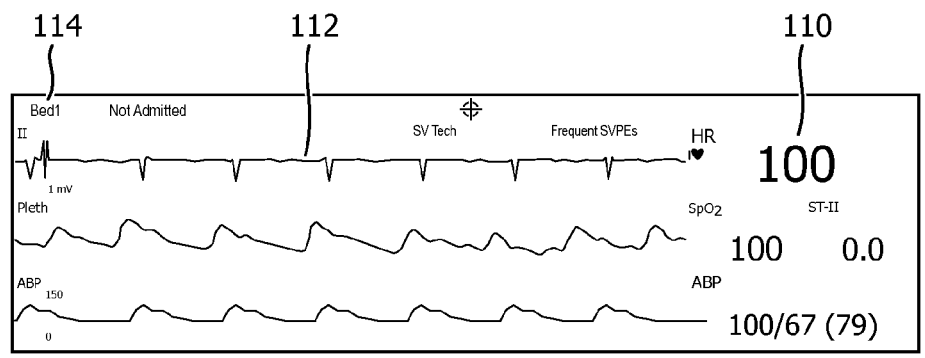
Figure 9:
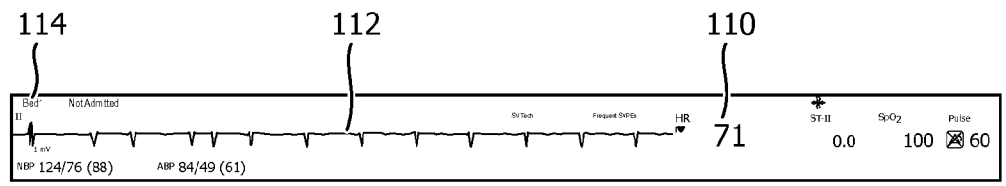

With reference to FIGS. 3-5, a plurality of numeric tiles 100 are displayed in sectors 102 of the patient information displays. The sectors 102 contain three numeric tiles 100 larger than any others, up to twice as tall depending on what will fit (and proportionally wider, or as wide as will fit). This is because in the majority of patients, the caregivers are primarily interested in heart rate, SpO2 and a pressure. All other numeric tiles 100 are shown around the first three with highest priority at the top and then moving left to right and top to bottom depending on the space available.

With reference to FIG. 6-9, a plurality of numeric 110 and wave tiles 112 are displayed in sectors 114 of the patient information display. This is the most common view of the data with waves 112 and numeric 110 tiles. If the sector is too small to show 3 seconds of wave tile along with 2 numeric tiles, the sector reverts to the "Numerics Only". Wave tile 112 are in the top left of the sector 114 stacked vertically. The wave tiles 112 are as long as they can be (3, 6 or 10 cycles) while still allowing 2 numeric tiles 110 to fit next to each other to the right of each wave tile 112. The sector 114 shows as many wave tiles 112 as are available or will fit when stacked vertically. "Aligned Numerics" (numeric tile that are associated with a wave e.g. an arterial blood pressure (ABP) numeric which is associated with an ABP wave tile) are shown next to the associated wave tile 112. These numeric tiles 110 are slightly larger than other numeric tiles 114. The Heart Rate numeric tile is even larger than other aligned numeric tiles, taking up the space of 2 numeric tiles next to the first wave tile. Any space around the aligned numeric tiles 110 is filled in with numeric tiles 110 with the highest priority at the top. Any space underneath the wave tiles 114 (if the space available is at least the minimum height of a numeric) are also filled with numeric tiles 110 with the highest priority at the top left going right and then down.

Figure 10:
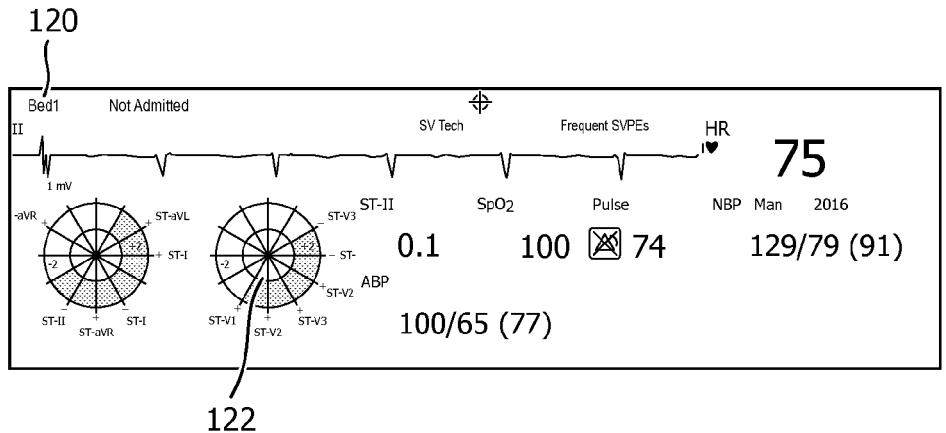
FIG. 10-13 illustrate examples of ST Map sectors of a patient information display system in accordance with the present application.
Figure 11:
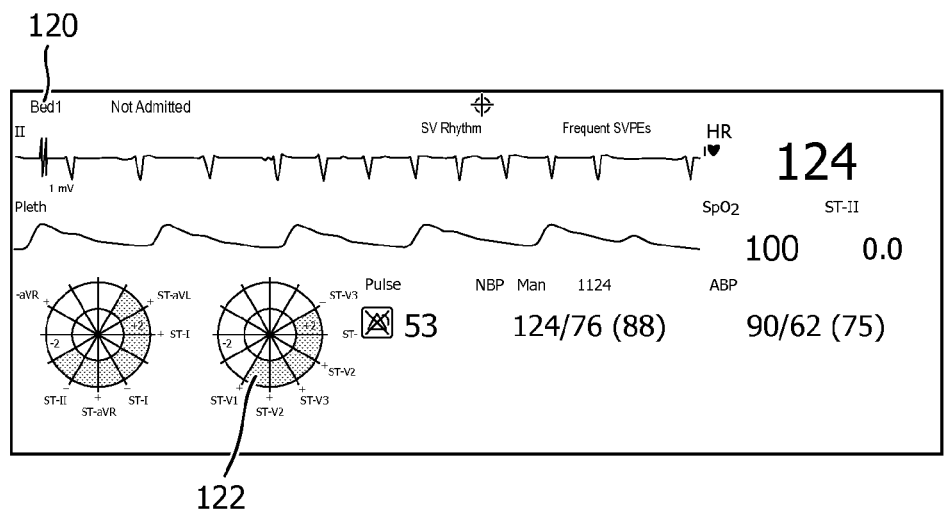

With reference to FIGS. 10 and 11, a plurality of sectors 120 including ST Map tiles 122 used for cardiac assessment are illustrated. The ST Map tile 122 is like a "Basic View" except that the ST Map tile 122 replaces the space taken by the bottom 2 waves in the sector. Because it is clinically important to show a primary ECG wave when doing cardiac assessment, this view is only available when 3 waves can fit in a sector (1 primary ECG wave and 2 waves that can be replaced by ST Map). If this requirement is not met, the layout defaults to the "Basic View".

Figure 12:
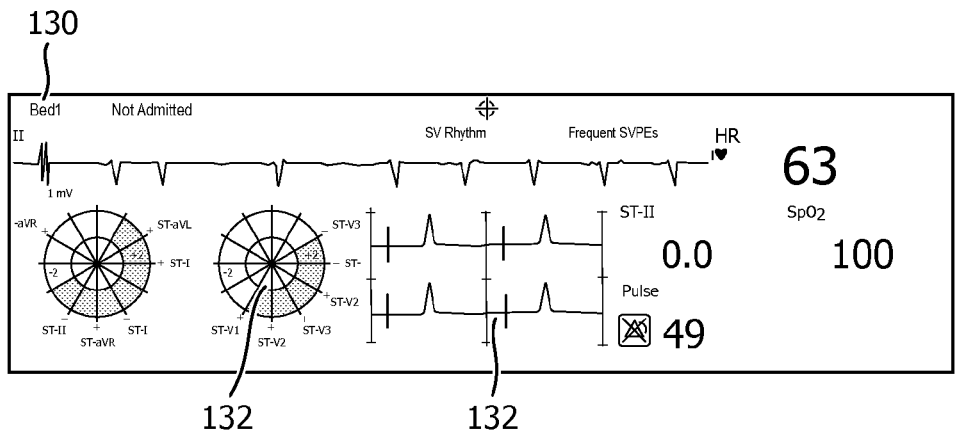
Figure 13:
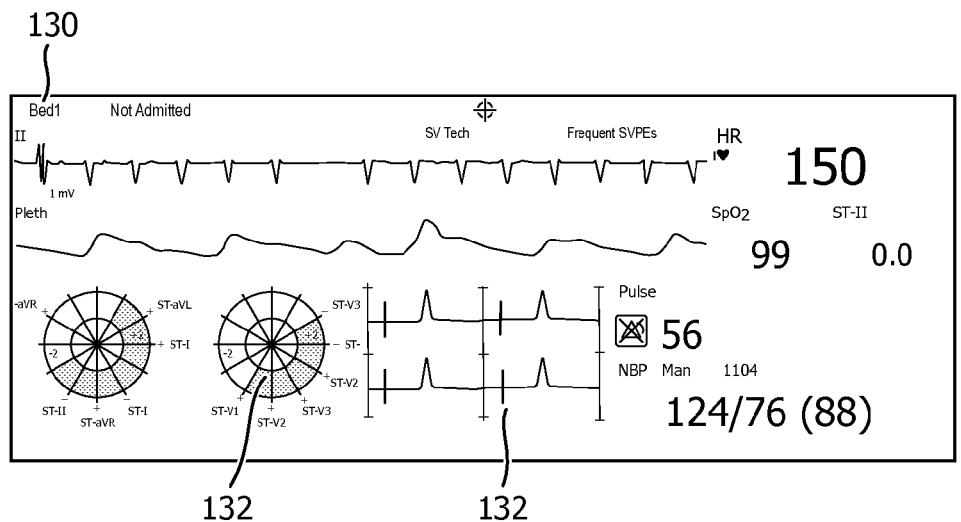

With reference to FIGS. 12 and 13, a plurality of sectors 130 including ST Map tiles 132 with snippet tiles 134 used for cardiac assessment are illustrated. ST Snippet tiles 134 are snapshots of an ECG beat also used for cardiac assessment. This view is defined by the following non exclusive exemplary rules: This is like the "ST Map" except that snippet tiles are shown to the right of the ST Map tile. As with "ST Map", this view is only available when 3 waves can fit in a sector. This actually encompasses 3 separate layouts: "ST Map and Lateral Snippets", "ST Map and Inferior Snippets", and "ST Map and Anterior Snippets" so the user can choose which snippet tiles to show. The ST Map illustrates operational limits, or STEMI limits based on patient gender and current evidence based guidelines.

Figure 14:
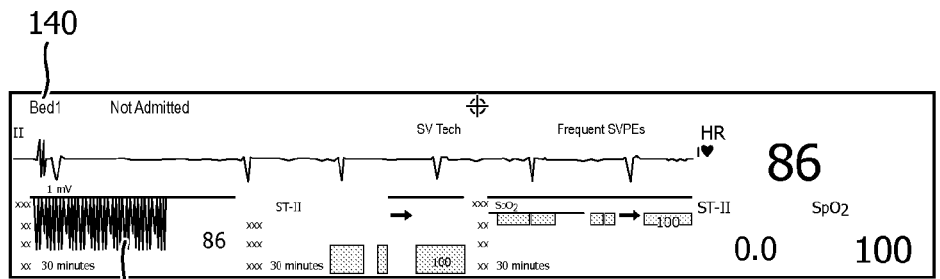
FIGS. 14-16 illustrate examples of trend sectors of a patient information display system in accordance with the present application.
Figure 15:
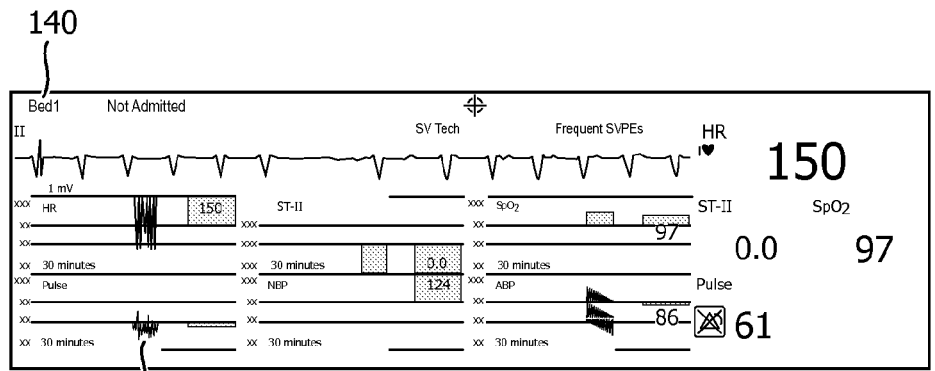
Figure 16:
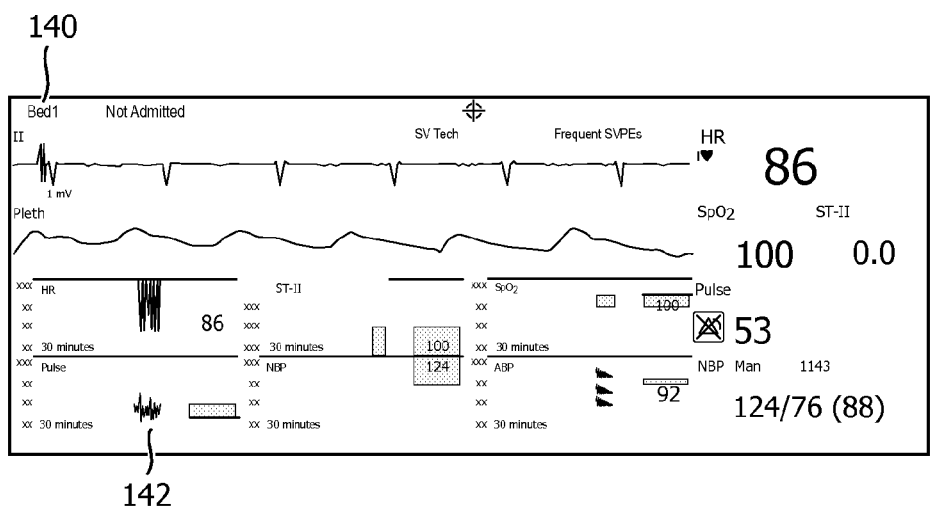
Figure 17:
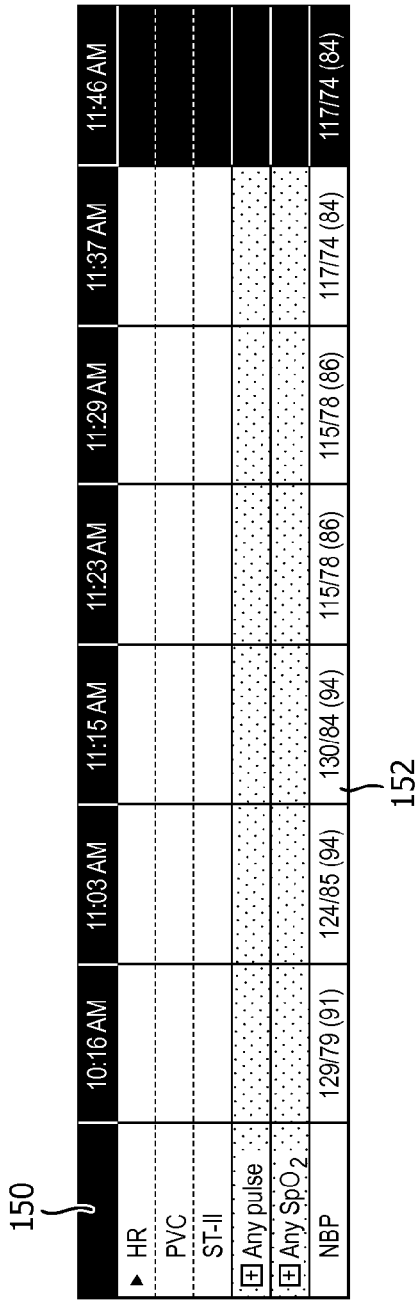
FIG. 17-19 illustrate examples of historical numeric data sectors of a patient information display system in accordance with the present application.
Figure 18:
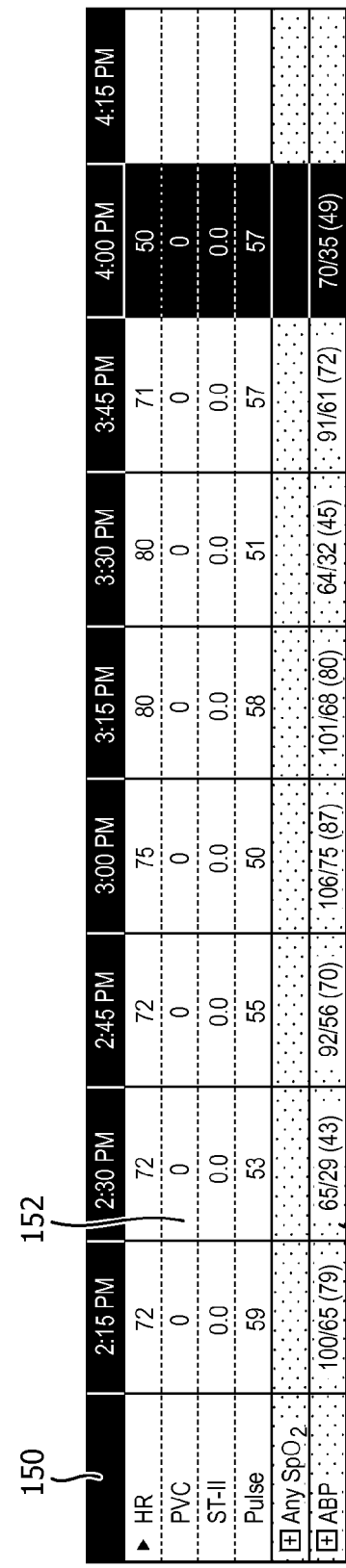
Figure 19:
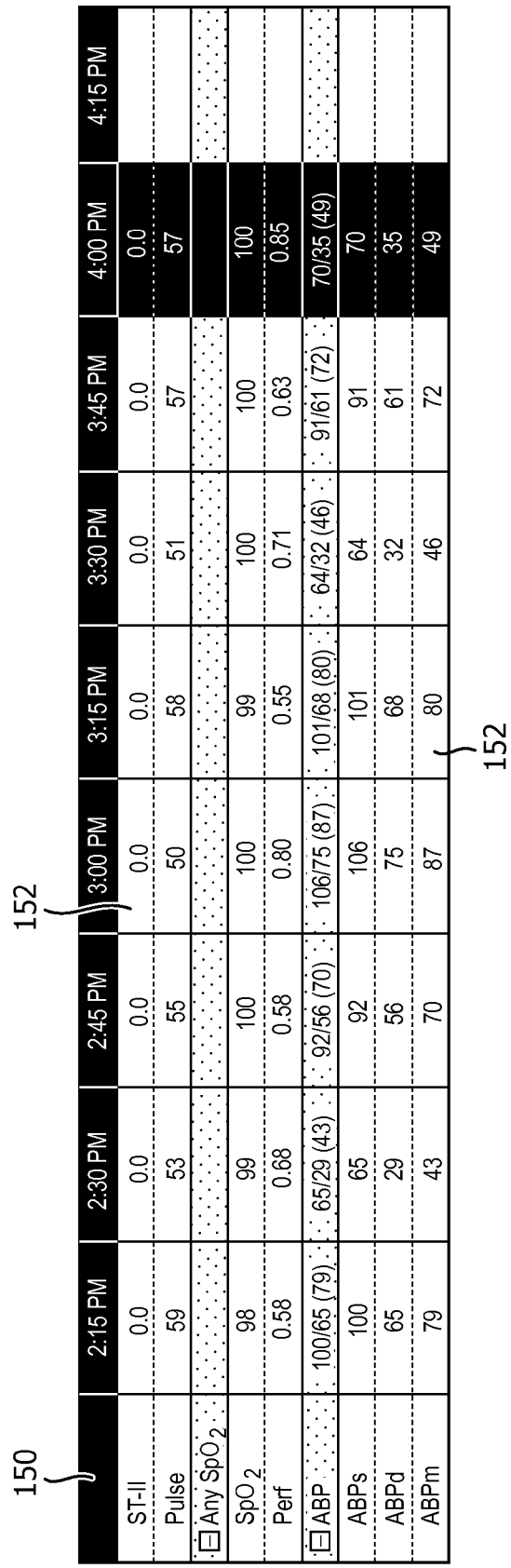

With reference to FIGS. 14-16, a plurality of sectors 140 including trend tiles 142 are illustrated. Trend tiles 142 are used to show the history of physiological signs over time. This view is defined by the following rules: This is like the "Basic View" except that up to 2 of the bottom wave tiles are replaced by trend tiles 142. A primary ECG wave tile often has the highest priority, so if 2 wave tiles fit in the sector, only 1 of those is replaced by trend tile 142. If 3 or more wave tiles fit, the bottom 2 wave tiles are replaced. If more than 1 wave tile cannot fit, this view defaults to the "Basic View". Multiple trend tiles 142 can fit in the space of a single wave tile, depending on the width of that wave tile. With reference to FIG. 17-19, a plurality of sectors 150 including historical data tiles 152 are illustrated. The sectors 150 contain historical data tiles 152 depending on what will fit (and proportionally wider, or as wide as will fit). The highest priority historical data tiles 152 are shown at the top and then moving left to right and top to bottom depending on the space available.

Figure 20:
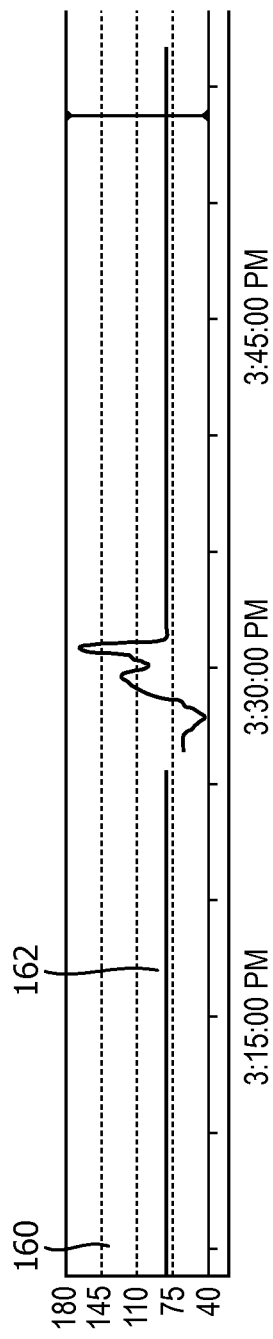
FIGS. 20-21 illustrate examples of historical trend sectors of a patient information display system in accordance with the present application.
Figure 21:
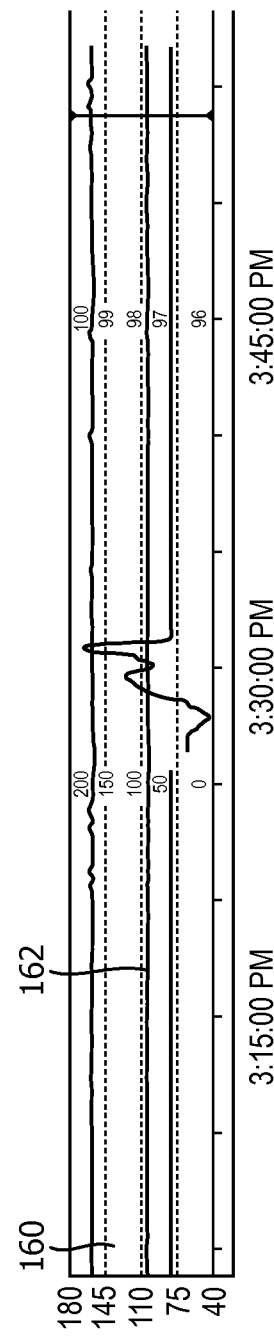

With reference to FIGS. 20-21, a plurality of sectors 160 including historical trend tiles 162 are illustrated. The historical trend tiles 162 are used to show the history of physiological signs over time. The highest priority historical trend tiles 162 are shown at the top and then moving to bottom depending on the space available.

Figure 22:
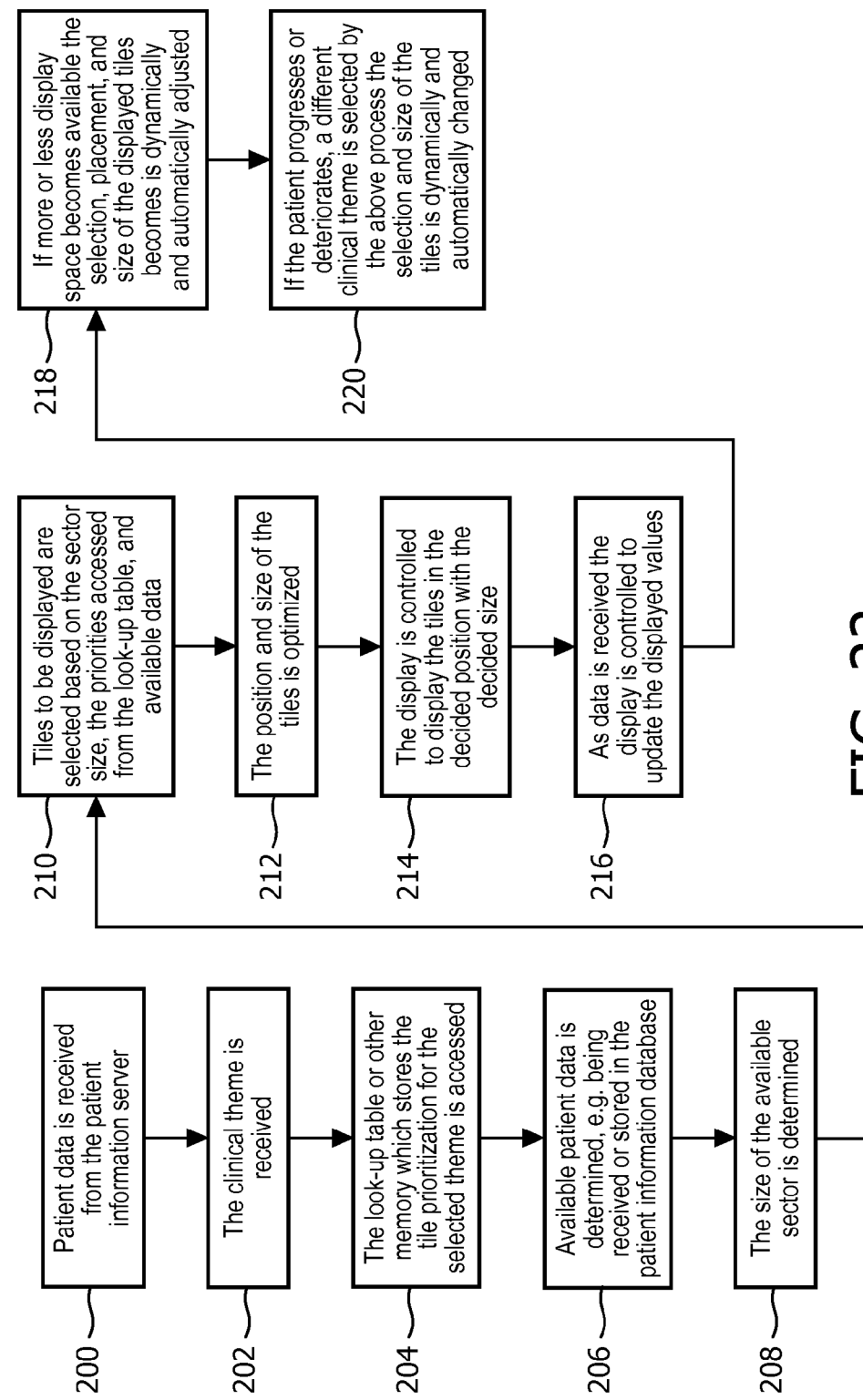
FIG. 22 is a flowchart diagram of the operation of the patient monitoring system in accordance with the present application.

FIG. 22 illustrates the core operation of the controller of the patient monitoring system. The controller 16, 28, 46 includes one or more processor or computer programmed to perform the following steps. More specifically, the controller receives patient data from the patient information server in a step 200. In a step 202, the controller receives the clinical theme. The controller accesses the look-up table or other memory which stores the tile prioritization for the selected theme in a step 204. In a step 206, the controller determines which patient data is available, e.g. being received or stored in the patient information database. At a step 208, the size of the available sector is determined. At a step 210, the tiles to be displayed are selected based on the sector size, the priorities accessed from the look-up table, and the available data. At a step 212, the position and size of the tiles is optimized. At 214, the display is controlled to display the tiles in the decided position with the decided size. As the data is received, or step 216, the display is controlled to update the displayed values. If more or less display space becomes available the selection, placement, and size of the displayed tiles becomes is dynamically and automatically adjusted as described above in a step 218. Similarly, if the patient progresses or deteriorates, a different clinical theme is selected by the above process the selection and size of the tiles is dynamically and automatically changed in a step 220. The selection or change in selection of the clinical theme can be manually selected or automatically selected based on location, patient diagnosis, or other records from the patient information database, data receives the received data values, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A patient monitoring station comprising:
a display configured to display a plurality of sectors, each sector corresponding to a patient and including one or more tiles in which patient data of the patient corresponding to the tile are displayed, each tile having a minimum size;
a look-up table configured to store a plurality of clinical themes, each clinical theme including a corresponding prioritized list of patient data in which each listed patient data is associated with a relative priority to the corresponding clinical theme;
an input configured to input a selection of a selected one of the clinical themes;
a controller configured to control the display to display patient data from the corresponding patient in tiles of the corresponding sector of the display, the controller programmed to or including means to:
determine which patient data in the corresponding prioritized list of the selected theme is available for the patient for display,
populate the tiles of the corresponding sector with the patient data with the priority according to the selected clinical theme, and
adjusting a number and size of the tiles to fill and populate the corresponding sector with tiles with highest priority available patient data.

2. The patient monitoring station according to claim 1, wherein the controller is further programmed to automatically re-populate the tiles of at least one of the sectors of the display in real time as the clinical theme is changed to a new theme with the size and number of the tiles adjusted to display the highest priority available patient data of the new theme.

3. The patient monitoring station according to claim 1, wherein the controller is further programmed to or includes means to:
select tiles to populate the sector based on a size of the sector, the priority of the tiles to the selected clinical theme, and the available patient data from the prioritized list of patient data of the selected clinical theme.

4. The patient monitoring station according to claim 1, wherein the controller is further programmed to or includes means to:
dynamically adjust the number, placement, and size of the displayed tiles if more or less sector space becomes available.

5. A patient monitoring station comprising:
a display that displays a plurality of sectors, each sector including one or more tiles;
a controller configured to display patient data received from a patient information server in a corresponding sector of the display, the controller programmed to or including means to:
populate the tiles of the sectors with patient data according to a selected clinical theme wherein the clinical theme is based on at least one of a body system, disease, concept of interest, patient location, attending clinician, disease state, and treatment regimen, and
select the tiles based on a tile prioritization for each of the clinical themes, wherein for each clinical theme, a series of tile allocations is prioritized in a look-up table, wherein each tile has a maximum size and a minimum size to allow the controller to determine a layout of the sector.

6. The patient monitoring station according to claim 5, wherein the controller is further programmed to adjust both a number and the size of the displayed tiles of the sectors to optimize space available in the sectors.

7. The patient monitoring station according to claim 5, wherein each theme includes a prioritized list of patient data from highest priority patient data to lowest priority patient data and wherein the controller is further programmed to or includes means to:
for the selected theme, determine which patient data in the selected theme's prioritized list is available from the patient information server;
determine the minimum tile sizes of tiles corresponding to the available patient data;
determine whether tiles of the available patient data of the minimum tile size fit in the sector; and
if the tiles of the minimum tile size do not fit,
controlling the display to display the highest priority tiles which fit, and
if tiles of the minimum tile size do fit and do not fill the sector, controlling the display to enlarge one or more of higher priority tiles and display the available tiles with the one or more higher priority tiles enlarged.

8. The patient monitoring station according to claim 5, wherein each clinical theme includes a prioritization of tiles to populate the plurality of sectors, the tiles being prioritized based on the relevancy to the clinical theme.

9. The patient monitoring station according to claim 5, wherein the controller is further programmed to or includes means to:
dynamically change the clinical theme if the patient progresses or deteriorates and adjust the selection, placement, and size of the displayed tiles.

10. A patient monitoring system, the system comprising:
the patient information server;
one or more patient monitoring stations according to claim 5.

11. A method of displaying medical parameters, the method comprising:
in a look-up table, storing a plurality of clinical themes, each clinical theme including a corresponding prioritized list of patient data in which each listed patient data is associated with a priority indicating relevance to the corresponding clinical theme;
selecting a selected one of the clinical themes;

determining which patient data in the corresponding prioritized list of the selected theme is available for display;

controlling a display to display a plurality of sectors, each sector corresponding to a patient and including one or more tiles in which the available patient data of the patient corresponding to the tile is displayed;

populating the tiles of the corresponding sector with the patient data in accordance with the selected clinical theme; and, adjusting at least one of a number and size of the displayed tiles to fill the corresponding sector with the highest priority patient data.

12. The method according to claim 11, further including:
resizing the tiles for space available in the sector to optimize a number and size of displayed tiles in response to a change in the selected clinical theme.

13. The method according to claim 11, wherein the patient data includes at least one of current monitored physiological data and historical physiological data.

14. The method according to claim 11, wherein the clinical theme is based on at least one of a body system, disease, concept of interest, patient location, attending clinician, disease state, and treatment regimen.

15. The method according to claim 11, further including:
dynamically adjusting a selection, placement, and size of the displayed tiles if more or less sector space becomes available.

16. The method according to claim 11, further including:
dynamically changing the clinical theme in response to patient progress or deterioration and adjusting a selection, placement, and size of the displayed tiles.

17. A non-transitory computer readable medium containing software which, when loaded into a processor, programs the processor to perform the method according to claim 11.

18. A patient monitoring station comprising:
a display;
an input via which physiological data is received; and
one or processors programmed to perform the method according to claim 11.

19. The method according to claim 11, wherein the tiles have a minimum tile size and further including determining whether tiles of the minimum tile size with the available patient data from the prioritized list of patient data corresponding to the selected theme fit in the corresponding sector;

if all of the tiles of the minimum tile size do not fit, controlling the display to display only a portion of the tiles with the highest priority until the sector is filled; and if the tiles of the minimum tile size do fit and do not fill the sector, enlarging one or more of the highest priority tiles on the display.

* * * * *